United States Patent
Hijlkema et al.

(10) Patent No.: US 7,632,298 B2
(45) Date of Patent: Dec. 15, 2009

(54) DELIVERY SYSTEM FOR ENDOLUMINAL IMPLANT

(75) Inventors: Lukas J. Hijlkema, Moycullen (IE); Fionnan Friel, Barna (IE); Michael McMahon, Glin (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 935 days.

(21) Appl. No.: 11/049,387

(22) Filed: Feb. 2, 2005

(65) Prior Publication Data

US 2005/0131514 A1 Jun. 16, 2005

Related U.S. Application Data

(63) Continuation of application No. 09/573,273, filed on May 18, 2000, now Pat. No. 6,858,034.

(60) Provisional application No. 60/134,971, filed on May 20, 1999.

(51) Int. Cl.
*A61F 2/06* (2006.01)
(52) U.S. Cl. ..................... 623/1.12; 606/194
(58) Field of Classification Search .............. 606/108, 606/151, 190, 191, 192; 623/1.11, 1.12
See application file for complete search history.

(56) References Cited

U.S. PATENT DOCUMENTS

| | | | |
|---|---|---|---|
| 4,950,227 A | | 8/1990 | Savin et al. |
| 5,026,377 A | | 6/1991 | Burton et al. |
| 5,201,757 A | * | 4/1993 | Heyn et al. .................. 606/198 |
| 5,201,901 A | | 4/1993 | Harada et al. |
| 5,480,423 A | | 1/1996 | Ravenscroft et al. |
| 5,484,444 A | | 1/1996 | Braunschweiler et al. |
| 5,520,645 A | | 5/1996 | Imran et al. |
| 5,556,413 A | | 9/1996 | Lam |
| 5,562,726 A | | 10/1996 | Chuter |

(Continued)

FOREIGN PATENT DOCUMENTS

EP 0 775 470 5/1997

(Continued)

OTHER PUBLICATIONS

International Search Report dated Sep. 12, 2000.

*Primary Examiner*—Michael J Milano
*Assistant Examiner*—Victor X Nguyen
(74) *Attorney, Agent, or Firm*—Brooks, Cameron & Huebsch, PLLC

(57) ABSTRACT

A delivery system for delivering an endoluminal implant to a distal deployment location inside a body lumen from a proximal access location outside the lumen. The system comprises the implant, a catheter, and a slidable sheath having an advanced position in which the sheath covers the implant and a retracted position in which the implant is exposed. The catheter comprises a stabilizer having a distal end adjacent the implant proximal end and/or a catheter tip attached to a central core slideably disposed relative to the implant and having a proximal end adjacent the implant distal end. The catheter tip proximal end and/or the stabilizer distal end comprises a docking section adapted to releasably engage a portion of the implant. Each docking section has an engagement geometry comprising a flared engagement surface that extends inside a short axial length of the implant or a pocket having a bottleneck geometry.

7 Claims, 3 Drawing Sheets

U.S. PATENT DOCUMENTS

| | | | |
|---|---|---|---|
| 5,591,222 A | 1/1997 | Susawa et al. | |
| 5,609,627 A | 3/1997 | Goicoechea et al. | |
| 5,683,451 A | 11/1997 | Lenker et al. | |
| 5,702,418 A | 12/1997 | Ravenscroft | |
| 5,709,703 A * | 1/1998 | Lukic et al. | 623/1.12 |
| 5,749,921 A | 5/1998 | Lenker et al. | |
| 5,755,777 A | 5/1998 | Chuter | |
| 5,824,037 A * | 10/1998 | Fogarty et al. | 623/1.13 |
| 5,824,040 A | 10/1998 | Cox et al. | |
| 5,824,041 A * | 10/1998 | Lenker et al. | 606/195 |
| 5,843,167 A | 12/1998 | Dwyer et al. | |
| 5,902,334 A | 5/1999 | Dwyer et al. | |
| 5,910,144 A | 6/1999 | Hayashi | |
| 5,944,726 A | 8/1999 | Blaeser et al. | |
| 5,954,729 A | 9/1999 | Bachmann et al. | |
| 5,968,068 A | 10/1999 | Dehdashtian et al. | |
| 5,976,155 A | 11/1999 | Foreman et al. | |
| 5,989,280 A | 11/1999 | Euteneuer et al. | |
| 6,077,295 A | 6/2000 | Limon et al. | |
| 6,077,297 A | 6/2000 | Robinson et al. | |
| 6,110,191 A | 8/2000 | Dehdashtian et al. | |
| 6,120,522 A | 9/2000 | Vrba et al. | |
| 6,214,036 B1 | 4/2001 | Letendre et al. | |
| 6,254,633 B1 * | 7/2001 | Pinchuk et al. | 623/1.3 |
| 6,258,099 B1 | 7/2001 | Mareiro et al. | |
| 6,264,683 B1 | 7/2001 | Stack et al. | |
| 6,302,906 B1 | 10/2001 | Goicoechea et al. | |
| 6,319,275 B1 | 11/2001 | Lashinski et al. | |
| 6,395,017 B1 | 5/2002 | Dwyer et al. | |
| 6,500,202 B1 | 12/2002 | Shaolian et al. | |
| 6,607,551 B1 | 8/2003 | Sullivan et al. | |
| 6,858,034 B1 * | 2/2005 | Hijlkema et al. | 606/108 |
| 7,435,253 B1 * | 10/2008 | Hartley et al. | 623/1.12 |
| 2004/0204749 A1 | 10/2004 | Gunderson | |
| 2004/0236406 A1 | 11/2004 | Gregorich | |

FOREIGN PATENT DOCUMENTS

| | | |
|---|---|---|
| EP | 0 834293 | 4/1998 |
| WO | WO 94/15549 | 7/1994 |
| WO | WO 95/33422 | 12/1995 |
| WO | WO 98/53761 | 12/1998 |

* cited by examiner

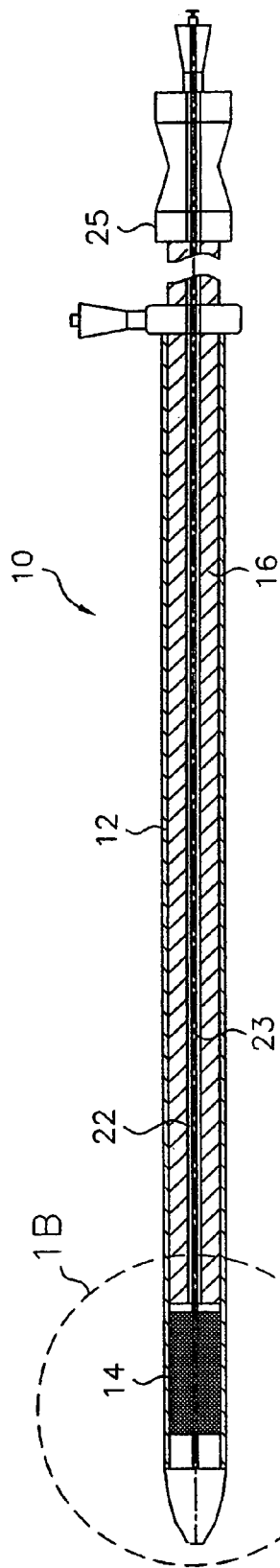
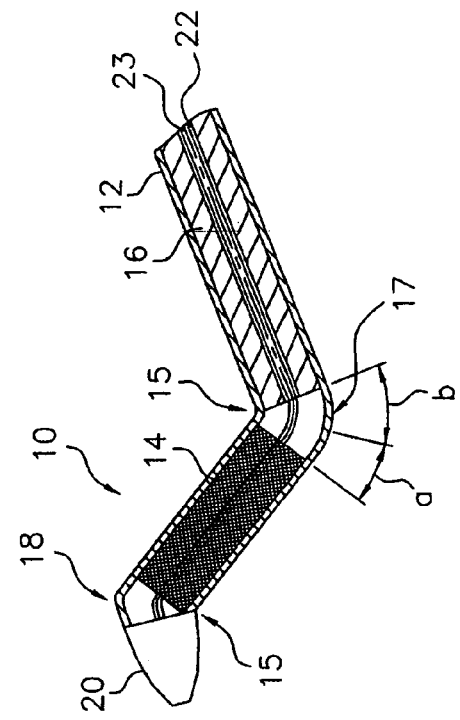
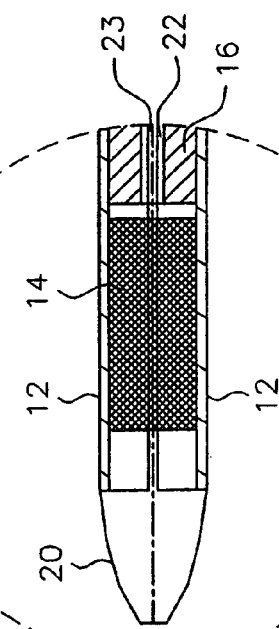
FIG. 1A (Prior Art)
FIG. 1B (Prior Art)
FIG. 2 (Prior Art)

DELIVERY SYSTEM FOR ENDOLUMINAL IMPLANT

CROSS-REFERENCE TO RELATED APPLICATIONS

This application is a continuation of U.S. patent application Ser. No. 09/573,273, filed May 18, 2000, now U.S. Pat. No. 6,858,034 which claims priority from U.S. Provisional Patent Application Ser. No. 60/134,971, filed on May 20, 1999, both of which are herein incorporated by reference.

TECHNICAL FIELD

The present invention relates generally to endoluminal grafts or "stents" and, more specifically, to stent delivery systems or "introducers".

BACKGROUND OF THE INVENTION

A stent is an elongated device used to support an intraluminal wall. In the case of a stenosis, a stent provides an unobstructed conduit for blood in the area of the stenosis. Such a stent may also have a prosthetic graft layer of fabric or covering lining the inside or outside thereof, such a covered stent being commonly referred to in the art as an intraluminal prosthesis, an endoluminal or endovascular graft (EVG), or a stent-graft. As used herein, however, the term "stent" is a shorthand reference referring to a covered or uncovered such stent.

A stent may be used, for example, to treat a vascular aneurysm by removing the pressure on a weakened part of an artery so as to reduce the risk of rupture. Typically, an intraluminal stent is implanted in a blood vessel at the site of a stenosis or aneurysm endoluminally, i.e. by so-called "minimally invasive techniques" in which the stent, restrained in a radially compressed configuration by a sheath or catheter, is delivered by a stent deployment system or "introducer" to the site where it is required. The introducer may enter the body through the patient's skin, or by a "cut down" technique in which the entry blood vessel is exposed by minor surgical means. When the introducer has been threaded into the body lumen to the stent deployment location, the introducer is manipulated to cause the stent to be ejected from the surrounding sheath or catheter in which it is restrained (or alternatively the surrounding sheath or catheter is retracted from the stent), whereupon the stent expands to a predetermined diameter in the vessel into the deployment location, and the introducer is withdrawn. Stent expansion may be effected by spring elasticity, balloon expansion, or by the self-expansion of a thermally or stress-induced return of a memory material to a pre-conditioned expanded configuration.

Referring now to FIGS. 1A and 1B, there is shown a prior art, pre-loaded stent delivery system 10 for housing and deploying a compressed stent 14. Stent delivery system 10 comprises an outer sheath 12 and a conventional pusher or stabilizer 16 loaded proximal to the stent. As used herein, the term "proximal" refers to the end closer to an access location outside the body whereas "distal" refers to the farther from the access location. Delivery system 10 also typically comprises a catheter tip 20 at the distal end and a pusher handle 25 located at the proximal end outside the body lumen. The catheter tip may be attached to central core 23 that runs through central lumen 22 within pusher 16. Central core 23 may guide the delivery system through the body lumen over a guidewire (not shown) to the area to be repaired, or may be adapted for inflating a balloon (if applicable), and/or for flushing the system. The delivery system may additionally have radiopaque markers at selected locations therein to be used for fluoroscopic guidance of the system through the body lumen.

To deploy stent 14, delivery system 10 is threaded through the body lumen to the desired location for stent deployment. Outer sheath 12 is then retracted, and pusher 16 acts as a stabilizer to keep stent 14 from retracting with the sheath. As outer sheath 12 retracts, stent 14 is exposed and expands into place against the body lumen to be repaired. The stent may be a self-expanding stent, such as a stent made of shape-memory nitinol (nickel-titanium) wire as are well-known in the art, or the stent may require inflation of a balloon to expand it against the walls of the body lumen, as is also well-known in the art.

Regardless of the type of stent or delivery system, the portion of delivery system 10 that houses compressed stent 14 typically has increased mass and rigidity as compared to the rest of delivery system 10. Thus, referring now to FIG. 2, when introducing delivery system 10 through tortuous anatomy, kinking of the delivery system may occur in region 17 of the system where pusher 16 and stent 14 interface, due to the rigidity of both the stent and the pusher. Kinking along kink angle "a" may develop as a result of the rigidity of compressed stent 14, whereas kinking along kink angle "b" may develop as a result of the rigidity of pusher 16. The resulting kink angle a+b is therefore dependent upon the material properties of both the compressed stent 14 and pusher 16. Similar kinking may also occur in region 18 where stent 14 and tip 20 interface.

Such kinking may prevent or hamper proper deployment of stent 14 because creases 15 that develop where sheath 12 is bent may prevent retraction of the sheath. Such creases 15 present a problem not only where stent 14 is intended for deployment in the tortuous portion of the body lumen, but also may persist even after the delivery system 10 is ultimately navigated past the tortuous portion of the lumen to a remote deployment site. Also, the discontinuity of the contact surface between stent 14 and pusher 16 could lead to an improper or inaccurate deployment of the stent. Where kinking causes such creases 15 in sheath 12 that prevent deployment, delivery system 10 must be retracted from the body and discarded, and the introduction process must start again with a new introducer. Thus, there is a need in the art to prevent such kinking in stent delivery systems.

SUMMARY OF THE INVENTION

One aspect of the invention comprises a delivery system for delivering a endoluminal implant to a distal deployment location inside a body lumen from a proximal access location outside the body lumen. The delivery system comprises the implant having a proximal end and a distal end; a catheter comprising at least one of a stabilizer having a distal end located adjacent the implant proximal end, a catheter tip attached to a central core slideably disposed relative to the implant and having a proximal end located adjacent the implant distal end, or a combination thereof; and a slidable sheath having an advanced position in which the sheath covers the implant and a retracted position in which the implant is exposed. At least one of the catheter tip proximal end or the stabilizer distal end comprises a docking section adapted to releasably engage a portion of the implant, each docking section comprising an engagement geometry for engaging the implant, each docking section engagement geometry comprising a flared engagement surface that extends inside a short axial length of the implant or a pocket having a bottleneck geometry.

Another aspect of the invention comprises a system for retaining a portion of a medical implant on a delivery member until performance of a predetermined release action. The system comprises the delivery member, comprising an outer sheath and an inner tubular member for engaging a portion of the implant, the sheath having an advanced position in which the sheath covers the implant, and a retracted position in which the implant is exposed. The inner tubular member has an axis and one or more flexible fingers, the one or more flexible fingers having an unrestrained configuration with the sheath in the retracted configuration in which the fingers are biased angularly outward from the inner tubular member axis, and a restrained configuration with the sheath in the advanced configuration in which the fingers are adapted to engage a portion of the implant. Each finger comprises an end member having a different cross sectional geometry than a remainder of the finger.

Yet another aspect of the invention comprises a delivery system for delivering an endoluminal implant, the delivery system comprising the implant having a proximal end and a distal end and a catheter comprising at least one of a stabilizer, a catheter tip, or a combination thereof, the stabilizer having a distal end located adjacent the implant proximal end, the catheter tip having a proximal end located adjacent the implant distal end and attached to a central core slideably disposed relative to the implant. At least one of the catheter tip proximal end or the stabilizer distal end comprises a docking section adapted to releasably engage a portion of the implant, the docking section comprising a pocket adapted to releasably contain a limited length of one end of the compressed implant inserted therein. The pocket comprises an annular pocket having an inner wall located radially inward of the compressed implant and an outer wall located radially outward of the compressed implant, the inner wall and the outer wall both terminating at a substantially same axial location relative to the implant.

Still another aspect of the invention comprises a delivery system comprising the implant; a catheter comprising at least one of a stabilizer having a distal end located adjacent the implant proximal end and/or a catheter tip attached to a central core slideably disposed relative to the implant and having a proximal end located adjacent the implant distal end; and a slidable sheath having an advanced position in which the sheath covers the implant and a retracted position in which the implant is exposed. At least one of the catheter tip proximal end or the stabilizer distal end comprises a docking section adapted to releasably engage a portion of the implant, the docking section comprising an engagement geometry for engaging the implant, in which the docking section engagement geometry comprises (a) a pocket having an outer wall located radially outward of the compressed implant and (b) a radial protrusion that engages the implant. In one embodiment, the docking section radial protrusion protrudes inward from the pocket outer wall. In another embodiment, the docking section pocket comprises a flared end rim radially biased outward relative to the compressed stent and adapted for the inward protrusion to releasably grip a limited length of the proximal end of the stent in pushing engagement therewith when the flared end rim is inwardly compressed by the sheath to a non-flared diameter.

It is to be understood that both the foregoing general description and the following detailed description are exemplary, but are not restrictive, of the invention.

BRIEF DESCRIPTION OF DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 1A is a longitudinal section schematic illustration of an exemplary stent delivery system of the prior art.

FIG. 1B is an enlarged portion of FIG. 1A.

FIG. 2 is a longitudinal section schematic illustration of an exemplary stent delivery system of the prior art in a kinked state due to the varying rigidity along the system.

DETAILED DESCRIPTION OF INVENTION

Figure 3:
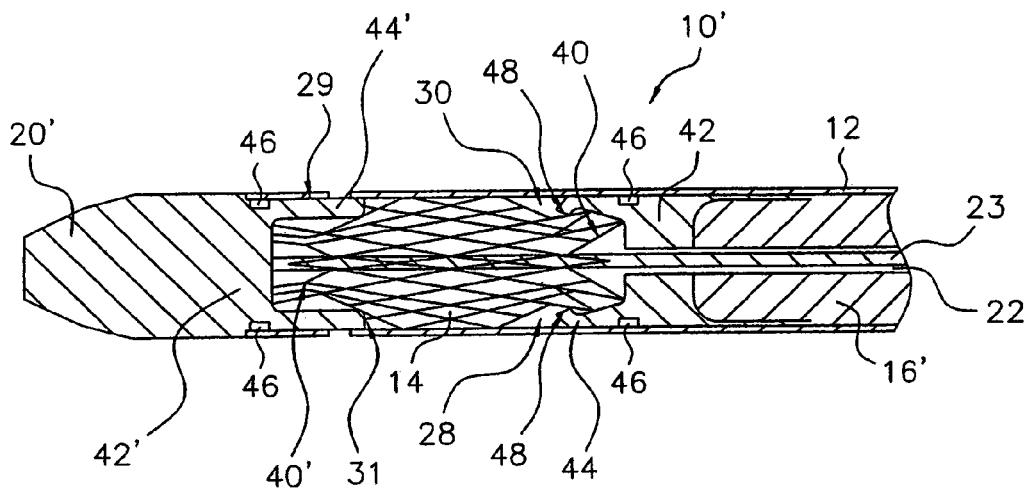
FIG. 3 is a longitudinal section schematic illustration of a portion of an exemplary stent delivery system of the present invention, showing the stent in a compressed state cradled in the docking section pockets of both the catheter tip and the pusher.
Figure 4:
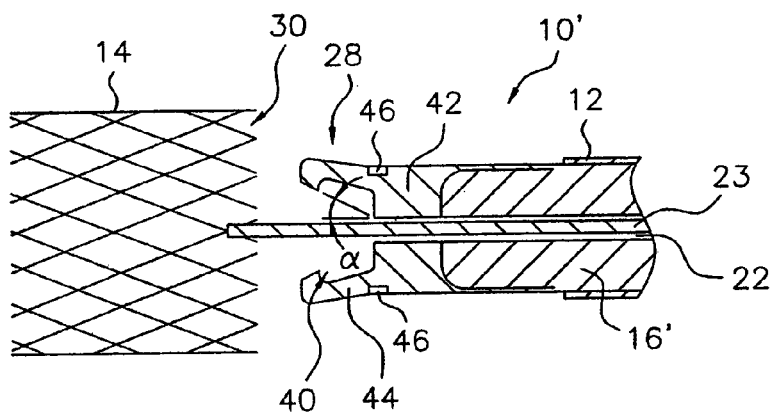
FIG. 4 is a longitudinal section schematic illustration of the pusher of FIG. 3 shown in a deployed state after retraction of the outer sheath.

Referring now to the drawing, wherein like reference numerals refer to like elements throughout, FIGS. 3-4 illustrate an exemplary stent delivery system 10' of the present invention, having an exemplary docking pusher 16' and docking catheter tip 20'. As shown in FIG. 3, stent delivery system 10' comprises an outer sheath 12, central lumen 22, and central core 23, similar to delivery systems known in the art. As used herein, the term "system" shall encompass both a completed assembly which is capable of deploying a stent or a sub-assembly which is capable of deploying a stent when combined with other components. Docking pusher 16' and catheter tip 20', however, comprise docking sections 42 and 42' respectively, each docking section having a pocket 40 and 40', respectively. Docking section 42 located at pusher distal end 28 is adapted to hold proximal end 30 of compressed stent 14, whereas docking section 42 located at catheter tip proximal end 29 is adapted to hold distal end 31 of compressed stent 14. Docking section 42 or 42' may be a discrete section connected to, respectively, pusher 16' or catheter tip 20', as shown in FIGS. 3 and 4 with respect to pusher 16', or may be a hollowed section integral to the rest of the pusher or catheter tip, as shown in the figures with respect to catheter tip 20'.

Other docking section configurations or means for engaging the compressed stent end with the pusher or catheter tip may also be used, as described herein later.

The term "pusher" is used herein throughout, although such device may also be referred to in the art as a "stabilizer", because the method of deploying the stent may not actually comprise "pushing" the stent out of the sheath, but rather "stabilizing" the stent (holding it in place and preventing it from moving) while the outer sheath is retracted. Thus, use of the term "pusher" herein refers to such a device adapted for any method of deploying known in the art, including as a stabilizer, and the term "pusher" is not intended as a limitation thereof.

Docking pusher 16' and docking catheter tip 20' overcome kinking in the body lumen because a certain amount of compressed stent 14 is actually docked or cradled inside pocket 40 or 40', creating a smooth transition between the stent and the pusher or catheter tip. The pusher and stent and/or catheter tip and stent in such docked configurations thus move together at their respective interface points while navigating the tortuous anatomy of the body lumen, by minimizing any area of weakened rigidity to prevent kinks.

In addition, as long as rim 44 of docking section 42 in pusher 16' grips stent 14, the stent may be "recaptured" or "recovered" even once it has been partially deployed. For instance, if a medical professional determines that a partially deployed stent 14 needs to be repositioned, pusher 16' may be pulled back within sheath 12 or the sheath advanced to recover the partially deployed stent. Then, the deployment process can start over. Other embodiments having other means for releasably engaging the stent may offer similar recapture capabilities.

Also, because of the docked arrangement between stent 14 and pusher 16', the stent may be rotated, pushed, or pulled both before and during deployment, unlike with conventional deployment systems where the pusher can only transmit force in a pushing direction. For example, where the stent architecture has a particular feature intended for alignment with a particular part of the body lumen, such as a particularly flexible portion of the stent to be aligned with a tortuous portion of the body lumen, the stent can be rotated, pushed, or pulled to effect this alignment. Additionally, in the configuration shown in FIG. 3 where docking section 42 pinches stent 14 against central core 23, creating friction, there is less undesired movement of the stent inside the delivery system as compared to non-docked prior configurations. Additionally, the use of a docking section in the catheter tip may facilitate placement of the distal end of the stent in a predetermined location.

As shown in FIG. 3, stent 14 is held within pocket 40 of docking section 42 of pusher 16' and pinched inwardly by end rim 44. When compressed within sheath 12, docking section 42 has a bottleneck shape created by inward protrusions 48 of end rim 44 that define a neck with a smaller diameter than the remainder of pocket 40, as shown in FIG. 3. End rim 44 of docking section 42 thus has a normal radial bias outward that is compressed and confined within the walls of sheath 12 during introduction to the body. As shown in FIG. 4, once the target zone has been reached, outer sheath 12 is retracted. When sheath 12 is retracted beyond end rim 44 of docking section 42, rim 44 springs open into an outwardly flared configuration and releases proximal end 30 of stent 14. Accordingly, docking section 42 may comprise any material, such as stainless steel, that provides flared end rim 44 with the requisite "springiness" to pinch inward when compressed and to spring open when the sheath is retracted. Although illustrated with respect to the pusher docking section 42 in FIG. 4, this outwardly-flared configuration may also be applicable to catheter tip docking section 42'; however, as shown in FIG. 3, a non-outwardly-biased, cylindrical configuration is preferred, as described below.

Instead of having a bottleneck shape when compressed within sheath 12 and radially flared and biased outward when not housed within the sheath, end rim 44' of docking section 42' in catheter tip 20' is cylindrical in shape and capable of holding stent 14 within pocket 40' merely by frictional engagement. Prior to retraction of sheath 12 to deploy stent 14, central core 23 and tip 20' attached thereto may, in some cases, need to be advanced distally so that the stent disengages from the pocket 40'. Such a non-radially-biased pocket may also be provided on docking section 42 of pusher 16'. In such case, stent 14 may be partially deployed and anchored into the walls of a body lumen so that the stent has sufficient frictional resistance against the body lumen to enable pusher 16' to be retracted to disengage the stent from within the non-flared pocket without dislocating the stent.

The step of advancing catheter tip 20' prior to retraction of sheath 12 may also be performed to facilitate stent delivery even where docking section 42' includes a radially-biased end rim (not shown). Such a radially-biased end rim on catheter tip 20', however, may present difficulty in preparing delivery system 10' for retraction from the body after deployment unless there is some mechanism to re-compress the end rim back inside sheath 12. Without such re-compression of the radially-biased end rim back inside the sheath, such as is possible with respect to pusher 16' merely by retracting the pusher to pull end rim 44 back inside sheath 12, the radially-biased end rim may protrude from the streamlined shape of the delivery system at the catheter end during retraction and provide a catching point that may damage the body lumen. Thus, a non-radially-biased end rim 44' is preferred for catheter tip 20'.

Docking section 42 may include a radiopaque marker 46, to provide increased radiographic "vision" of the pusher end, and when combined with a similar marker (not shown) on the proximal end of stent 14, to visualize relative movement of pusher and stent as stent 14 disengages from pusher 16'. Similar markers 46 may also be provided for similar purposes on the catheter tip docking section 42' and on the stent distal end (not shown). "Radiopaque marker" as used herein encompasses any discrete area of different radiopacity as compared to a surrounding area.

Pusher docking sections, catheter tip docking sections, stent delivery systems, and methods incorporating such pushers and/or catheter tips may take a wide variety of forms other than that described specifically above. A particular stent delivery system may include only a pusher docking section, only a catheter tip docking section, or both. The essence of any such docking section is that it releasably engages an end of the stent over some axial length in a manner whereby that engagement is releasable upon stent deployment. The term "releasably engaging" denotes that the engagement between the docking section and the stent is not permanent, but rather is releasable in the sense that the stent is released from the docking section when the outer sheath is retracted or when the pusher or catheter tip is advanced or retracted away from the stent. The pusher docking section is either biased radially outward or defines a pocket in which the portion of the stent proximal end is nested.

The length of the stent engaged by the docking section of this invention should be sufficiently long, taking into account the stent diameter and flexibility as well as the tortuosity of the lumen to be traversed during its deployment, to maintain a pushing engagement notwithstanding the tortuosity for which the stent is designed. Such pushing engagement enables transmission of a pushing force applied thereto, such as from the pusher to the stent, or from the stent to the catheter tip. The length of the stent engaged by the docking section should be sufficiently short, however, and/or the angle of radial flare a (as shown in FIG. 4) sufficiently great, so as to facilitate reliable release of stent 14 when sheath 12 is retracted. The dimensions and mechanical features of individual docking section designs may be readily determinable by those skilled in the art.

In particular, the docking section may comprise an axially-extending engagement surface which extends over a short axial length of the stent either on the interior or exterior thereof. Such surface may define the interior of pocket 40 previously described and shown in FIGS. 3 and 4, or an insert adapted to be inserted within the stent end to engage the stent end, as shown in FIG. 6.

Figure 6:
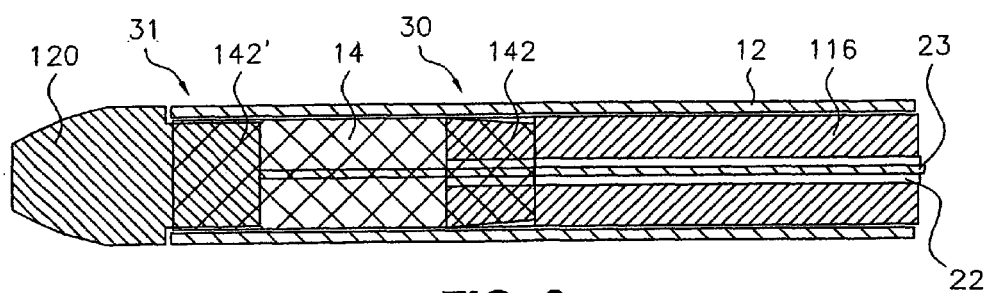
FIG. 6 a longitudinal section schematic illustration of exemplary docking sections of the present invention, showing the stent in a compressed state with a pusher docking section and a catheter docking section inserted in the ends thereof.

As shown in FIG. 6, docking section 142' of catheter tip 120 is a reduced diameter section (i.e., an insert) of catheter 120 that fits within distal end 31 of compressed stent 14. Docking section 142 of pusher 116 fits within proximal end 30 of compressed stent 14, and is radially biased outward to firmly hold stent 14 against sheath 12. Such bias outward to radially urge the stent proximal end 29 against the inner surface of the deployment sheath 12 further facilitates pusher 116 and stent 14 moving as one without pulling away from one another. Although docking section 142' having merely a reduced diameter section is illustrated in FIG. 6 with respect to catheter tip 120 whereas radially-biased-outward docking section 142 is illustrated with respect to pusher 116, either configuration is applicable to both the catheter tip and the pusher. As described above, however, a non-biased configuration is generally preferred at the catheter tip for ease of delivery system retraction.

Figure 7A:
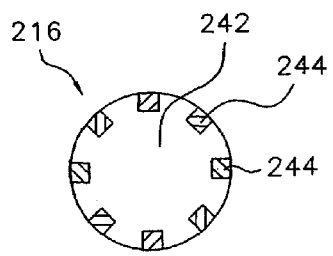
FIGS. 7A and 7B are an end view and a side view, respectively, of an exemplary docking section of the present invention comprising a set of fingers.
Figure 7B:
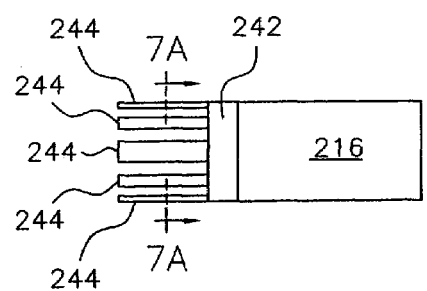
Figure 8A:
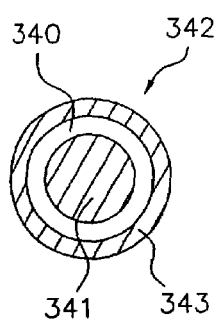
FIGS. 8A and 8B are an end view and a side view, respectively, of an exemplary docking section of the present invention comprising an annular pocket.
Figure 8B:
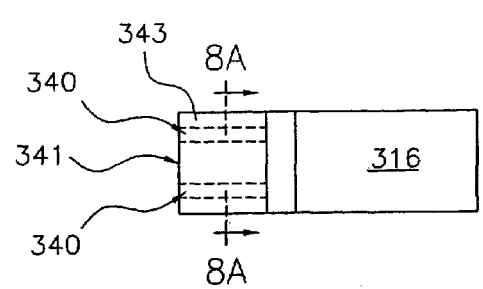
Figure 8C:
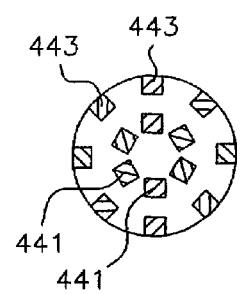
FIG. 8C is an end view of an exemplary docking section of the present invention, showing a docking section comprising an annular pocket defined by a plurality of fingers.

In another exemplary embodiment, shown in FIGS. 7A and 7B, docking section 242 of pusher 216 may comprise engagement means in the form of a set of fingers 244. Fingers 244 may define a pocket adapted for surrounding the stent, as shown in FIGS. 7A and 7B. Referring now to FIGS. 8A and 8B, in yet another embodiment, docking section 342 of pusher 316 may comprise pocket 340 in the form of an annular pocket between inner wall 341 and outer wall 343 adapted for insertion of the stent proximal end (not shown). Inner wall 341 may define a hollow or solid cylinder, or may be in the form of fingers that insert within the stent. Outer wall 343 may be solid as shown in FIGS. 8A and 8B, or may be in the form of outer fingers. As shown in FIG. 8C, another embodiment may comprise a plurality of inner fingers 441 and outer fingers 443 that define the inner wall and outer wall, respectively. Another embodiment, not shown, may comprise only inner fingers 441. Such inner fingers, outer fingers, or combination thereof may be radially biased outward. Although docking sections 242, 342, and 442 are described and shown in FIGS. 7A-8B with respect to pushers, similar docking section configurations may be provided for catheter tips.

The invention also comprises a method for pre-loading a stent delivery system, as described below relative to FIGS. 3 and 4. The method comprises loading at least compressed stent 14 and pusher 16' within outer sheath 12, including releasably engaging a portion of stent proximal end 30 with docking section 42 at pusher 16' distal end 28, stent distal end 31 with docking section 42' at catheter tip 20' proximal end 29, or a combination thereof. The method may include disposing a portion of the corresponding stent end 30 or 31 within a pocket 40 in docking section 42 or 42'.

Figure 5:
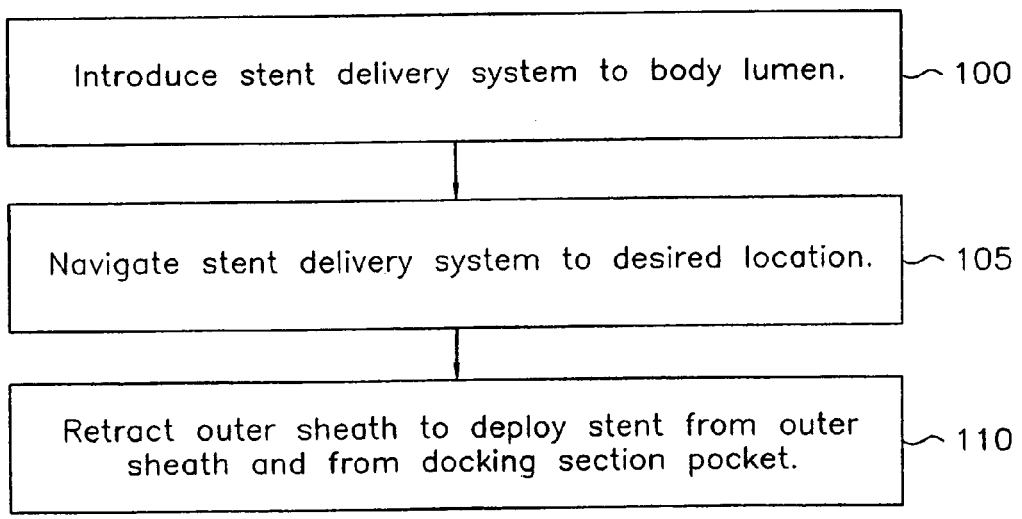
FIG. 5 is a flowchart depicting an exemplary method of deploying a stent in accordance with the present invention.

The invention further comprises a method for deploying a stent in accordance with the flowchart depicted in FIG. 5 and the drawings shown in FIGS. 3 and 4. The method comprises in step 100, introducing a pre-loaded stent delivery system 10' to a body lumen. Delivery system 10' comprises a compressed stent 14 having a proximal end 30 and a distal end 31, a pusher 16' having a distal end 28, a catheter tip 20' having a proximal end 29 and attached to a central core 23 slideably disposed within pusher 16'. At least one of pusher 16' or catheter tip 20' have a docking section 42 or 42' adapted to releasably engage the stent end over some length thereof, such as with pocket 40 and/or 40' within which the stent end is disposed. Outer sheath 12 overlies compressed stent 14, pusher 16', and each docking section 42 and/or 42'. Next, in step 105, the stent delivery system is navigated to a desired location for deploying stent 14, and finally, in step 110, outer sheath 12 is retracted to deploy the stent from the outer sheath and from docking section 42 and/or 42' into the desired location. Where catheter tip 20' has a docking section 42', the method may further comprise advancing central core 23 and the catheter tip 20' attached thereto prior to retracting sheath 12, to further facilitate release of stent 14 from the docking section. Where pocket 40 has an end rim 44 that is radially biased outward and adapted to be inwardly compressed to grip the stent end when loaded within outer sheath 12, as shown in FIGS. 3 and 4, the method may further comprise the end rim expanding outward during evacuation of the stent from the pocket. Where, as is shown in FIG. 6, docking section 142 and/or 142' comprise a reduced diameter section adapted for inserting within the end of stent 14, the method may further comprise the stent expanding away from the reduced diameter section.

While the present invention has been described with respect to specific embodiments thereof, it is not limited thereto. Therefore, the claims that follow are intended to be construed to encompass not only the specific embodiments described but also all modifications and variants thereof which embody the essential teaching thereof.

What is claimed:

1. A delivery system for delivering an endoluminal implant to a distal deployment location inside a body lumen from a proximal access location outside the body lumen, the delivery system comprising:

the implant having a proximal end and a distal end;

a catheter comprising, a catheter tip, the catheter tip having a proximal end located adjacent the implant distal end and attached to a central core slideably disposed relative to the implant;

the catheter tip proximal end comprising a docking section adapted to releasably engage a portion of the implant, the docking section comprising a pocket adapted to releasably contain a limited length of one end of the compressed implant inserted therein, the pocket comprising an annular pocket having an inner wall located radially inward of the compressed implant and an outer wall located radially outward of the compressed implant, the inner wall and the outer wall both terminating at a substantially same axial location relative to the implant.

2. The delivery system of claim 1, wherein the docking section is integral to the catheter tip.

3. The delivery system of claim 1, wherein the docking section is an attachment to the catheter.

4. The delivery system of claim 1 wherein the docking section comprises a set of fingers comprising an inner set of fingers that extend inside a short axial length of the stent, and an outer set of fingers that extend over a short axial length of the stent forming an annular region between inner and outer sets of fingers.

5. A delivery system for delivering an endoluminal implant to a distal deployment location inside a body lumen from a proximal access location outside the body lumen, the delivery system comprising:

the implant having a proximal end and a distal end;

a catheter comprising, a catheter tip, the catheter tip attached to a central core slideably disposed relative to the implant and having a proximal end located adjacent the implant distal end;

the catheter tip proximal end comprising a docking section adapted to releasably engage a portion of the implant, the docking section comprising an engagement geometry for engaging the implant, and;

a slidable sheath having an advanced position in which the sheath covers the implant and a retracted position in which the implant is exposed;

the docking section engagement geometry comprising (a) a pocket having an outer wall located radially outward of the compressed implant and (b) a radial protrusion that engages the implant.

6. The delivery system of claim 5, wherein the docking section radial protrusion protrudes inward from the pocket outer wall.

7. The delivery system of claim 6, wherein the docking section pocket comprises a flared end rim radially biased outward relative to the compressed stent and adapted for the inward protrusion to releasably grip a limited length of the proximal end of the stent in pushing engagement therewith when the flared end rim is inwardly compressed by the sheath to a non-flared diameter.

* * * * *